(12) United States Patent
Klein

(10) Patent No.: US 7,803,535 B2
(45) Date of Patent: Sep. 28, 2010

(54) POLYMORPHISMS IN THE NOD2/CARD15 GENE

(76) Inventor: Hanns-Georg Klein, Labor Für Medizinische Genetik Dr. Klein, Lochhamer Str. 29, 82152 Martinsried (DE)

( * ) Notice: Subject to any disclaimer, the term of this patent is extended or adjusted under 35 U.S.C. 154(b) by 447 days.

(21) Appl. No.: 10/594,256

(22) PCT Filed: Mar. 29, 2005

(86) PCT No.: PCT/DE2005/000550

§ 371 (c)(1),
(2), (4) Date: Sep. 25, 2006

(87) PCT Pub. No.: WO2005/095640

PCT Pub. Date: Oct. 13, 2005

(65) Prior Publication Data

US 2007/0212694 A1    Sep. 13, 2007

(30) Foreign Application Priority Data

Mar. 27, 2004   (DE)   .................. 10 2004 015 143

(51) Int. Cl.
*C12Q 1/68*   (2006.01)
*C12P 19/34*   (2006.01)
*C07H 21/02*   (2006.01)
*C07H 21/04*   (2006.01)

(52) U.S. Cl. .................. 435/6; 435/91.2; 536/23.1; 536/24.3

(58) Field of Classification Search .................. None
See application file for complete search history.

(56) References Cited

OTHER PUBLICATIONS

Holler, E. et al., blood, vol. 107, pp. 4189-4193 (May 2006).*
Granell, M. et al., Haematologica, vol. 91, pp. 1372-1376 (2006).*
Brenmoehl, J. et al., Intensive Care Med., vol. 33, pp. 1541-1548 (2007).*
GenBank Accession No. AC007728 (Jun. 2001).*
GenBank Accession No. AQ534686 (May 1999).*

* cited by examiner

*Primary Examiner*—Teresa E Strzelecka
(74) *Attorney, Agent, or Firm*—J.C. Patents

(57) ABSTRACT

The present invention relates to methods as well as to nucleotide sequences used in these methods for prognosis and/or diagnosis of diseases associated with at least one of the polymorphisms Nod2-SNP8, Nod2-SNP12, Nod2-SNP13 in the NOD2/CARD15 gene.

8 Claims, 3 Drawing Sheets

Cumulative Incidence 1 year DIR HLA-identical siblings

Days after SCT

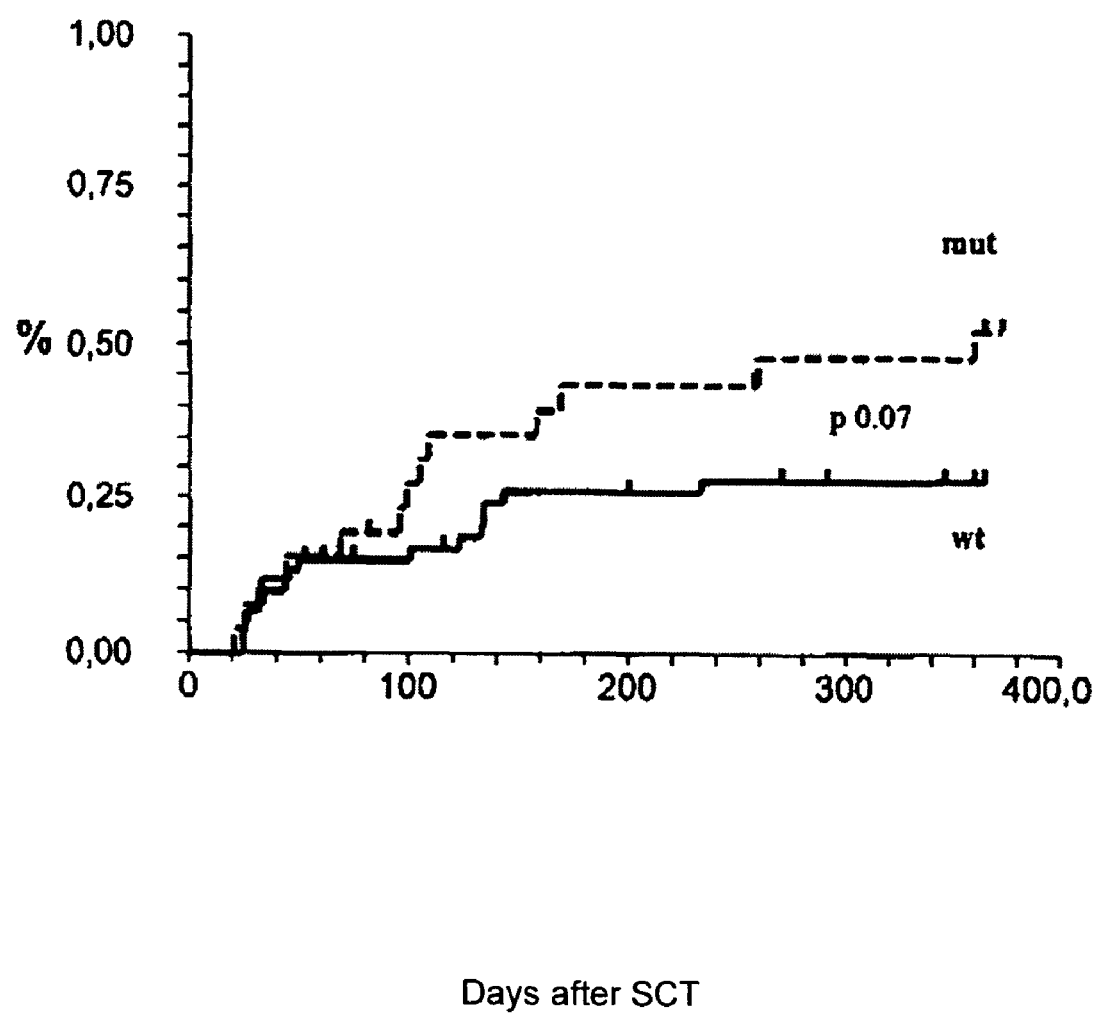

SEQUENCE LISTING

```
<160> NUMBER OF SEQ ID NOS: 13

<210> SEQ ID NO 1
<211> LENGTH: 20
<212> TYPE: DNA
<213> ORGANISM: Homo sapiens

<400> SEQUENCE: 1
ttcctggcag ggctgttgtc                                                    20

<210> SEQ ID NO 2
<211> LENGTH: 20
<212> TYPE: DNA
<213> ORGANISM: Homo sapiens

<400> SEQUENCE: 2
agtggaagtg cttgcggagg                                                    20

<210> SEQ ID NO 3
<211> LENGTH: 18
<212> TYPE: DNA
<213> ORGANISM: Homo sapiens

<400> SEQUENCE: 3
cctgctccgg cgccaggc                                                      18

<210> SEQ ID NO 4
<211> LENGTH: 18
<212> TYPE: DNA
<213> ORGANISM: Homo sapiens

<400> SEQUENCE: 4
cctgctctgg cgccaggc                                                      18

<210> SEQ ID NO 5
<211> LENGTH: 26
<212> TYPE: DNA
<213> ORGANISM: Homo sapiens
```

-continued

```
<400> SEQUENCE: 5
actcactgac actgtctgtt gactct                                          26

<210> SEQ ID NO 6
<211> LENGTH: 20
<212> TYPE: DNA
<213> ORGANISM: Homo sapiens

<400> SEQUENCE: 6
agccacctca agctctggtg                                                 20

<210> SEQ ID NO 7
<211> LENGTH: 29
<212> TYPE: DNA
<213> ORGANISM: Homo sapiens

<400> SEQUENCE: 7
ttttcagatt ctggggcaac agagtgggt                                       29

<210> SEQ ID NO 8
<211> LENGTH: 27
<212> TYPE: DNA
<213> ORGANISM: Homo sapiens

<400> SEQUENCE: 8
ttcagattct ggcgcaacag agtgggt                                         27

<210> SEQ ID NO 9
<211> LENGTH: 26
<212> TYPE: DNA
<213> ORGANISM: Homo sapiens

<400> SEQUENCE: 9
gtccaataac tgcatcacct acctag                                          26

<210> SEQ ID NO 10
<211> LENGTH: 24
<212> TYPE: DNA
<213> ORGANISM: Homo sapiens

<400> SEQUENCE: 10
cttaccagac ttccaggatg gtgt                                            24

<210> SEQ ID NO 11
<211> LENGTH: 22
<212> TYPE: DNA
<213> ORGANISM: Homo sapiens

<400> SEQUENCE: 11
ccctcctgca ggcccttgaa at                                              22

<210> SEQ ID NO 12
<211> LENGTH: 21
<212> TYPE: DNA
<213> ORGANISM: Homo sapiens

<400> SEQUENCE: 12
cctcctgcag gcccttgaa a                                                21

<210> SEQ ID NO 13
<211> LENGTH: 4485
<212> TYPE: RNA
<213> ORGANISM: Homo sapiens
```

-continued

<400> SEQUENCE: 13

| | | | | | |
|---|---|---|---|---|---|
| guagacagau | ccaggcucac | caguccugug | ccacugggcu | uuuggcguuc | ugcacaaggc | 60
| cuacccgcag | augccaugcc | ugcucccca | gccuaauggg | cuuugauggg | ggaagaggggu | 120
| gguucagccu | cucacgauga | ggaggaaaga | gcaagugucc | uccucggaca | uucuccgggu | 180
| ugugaaaugu | gccucgcagga | ggcuuuucag | gcacagagga | gccagcuggu | cgagcugcug | 240
| gucucagggu | cccuggaagg | cuucgagagu | guccuggacu | ggcugcuguc | cugggagguc | 300
| cucuccuggg | aggacuacga | gggcuuccac | cuccugggcc | agccucucuc | ccacuuggcc | 360
| aggcgccuuc | uggacaccgu | cuggaauaag | gguacuuggg | ccugucagaa | gcucaucgcg | 420
| gcugcccaag | aagcccaggc | cgacagccag | uccccaagc | ugcauggcug | cugggacccc | 480
| cacucgcucc | acccagcccg | agaccugcag | agucaccggc | cagccauugu | caggaggcuc | 540
| cacagccaug | uggagaacau | gcuggaccug | gcaugggagc | gggguuucgu | cagccaguau | 600
| gaaugugaug | aaaucagguu | gccgaucuuc | acaccgucc | agagggcaag | aaggcugcuu | 660
| gaucuugcca | cggugaaagc | gaauggauug | gcugccuucc | uucuacaaca | uguucaggaa | 720
| uuaccaguccc | cauuggcccu | gccuuuggaa | gcugccacau | gcaagaagua | uauggccaag | 780
| cugaggacca | cggugucugc | ucagucucgc | uuccucagua | ccauaugaugg | agcagagacg | 840
| cucugccugg | aggacauaua | cacagagaau | guccuggagg | cugggcagaa | guggggcaug | 900
| gcuggaccccc | cgcagaagag | cccagccacc | cugggccugg | aggagcucuu | cagcacccccu | 960
| ggccaccuca | augacgaugc | ggacacugug | cugguggugu | gugaggcggg | caguggcaag | 1020
| agcacgcucc | ugcagcggcu | gcacuugcug | ugggcugcag | ggcaagacuu | ccaggaauuu | 1080
| cucuuugucu | ucccauucag | cugccggcag | cugcagugca | uggccaaacc | acucucugug | 1140
| cggacucuac | ucuuugagca | cugcuguugg | ccugauguug | gucaagaaga | caucuuccag | 1200
| uuacccuuug | accacccuga | ccgugugccug | uuaaccuuug | auggcuuuga | cgaguucaag | 1260
| uucagguuca | cggaucguga | acgccacugc | ucccgaccg | accccacccuc | uguccagacc | 1320
| cugcucuuca | ccuucugca | gggcaaaccug | cugaagaaug | cccgcaaggu | ggugaccagc | 1380
| cguccggccg | cugugucggc | guccucagg | aaguacaucc | gcaccgaguu | caaccucaag | 1440
| ggcuucucug | aacagggcau | cgagcuguac | cugaggaagc | gccaucauga | gcccgggguug | 1500
| gcggaccgcc | ucauccgccu | gcuccaagag | accucagccc | ugcacgguuu | gugccaccug | 1560
| ccugucuucu | cauggauggu | guccaaaugc | caccaggaac | uguugcugca | ggaggggggg | 1620
| ucccccaaaga | ccacuacaga | uauguaccug | cugauucugc | agcauuuucu | gcugcaugcc | 1680
| acccccccag | acucagcuuc | ccaaggcucu | ggaccagucc | uucuucgggg | ccgccucccc | 1740
| acccuccugc | accugggcag | acuggcucug | ugggggcugg | gcaugugcug | cuacguguuc | 1800
| ucagcccagc | agcuccaggc | agcacagguc | agcccugaug | acauuucucu | uggcuuccug | 1860
| gugcgugcca | aaggugucgu | gccagggagu | acggcgcccc | uggaauuccu | ucacaucacu | 1920
| uuccagugcu | cuuugccgc | guucuaccug | gcacucagug | cugaugugcc | accagcuuug | 1980
| cucagacacc | ucuucaauug | uggcaggcca | ggcaacucac | caauggccag | gcuccugccc | 2040
| acgaugugca | uccaggccuc | ggagggaaag | gacagcagcg | uggcagcuuu | gcugcagaag | 2100
| gccgagccgc | acaaccuuca | gaucacagca | gccuuccugg | cagggcuguu | gucccgggag | 2160
| cacugggggcc | ugcuggcuga | ugccagaca | ucugagaagg | cccugcuccg | gcgccaggcc | 2220
| ugugcccgcu | ggguucuggc | ccgcagccuc | cgcaagcacu | uccacuccau | cccgccagcu | 2280

```
gcaccggguq aggccaagag cgugcaugcc augcccgggu ucaucuggcu cauccggagc    2340
cuguacgaga ugcaggagga gcggcuggcu cggaaggcug cacguggccu gaauguuggg    2400
caccucaagu ugacauuuug cagugugggc cccacugagu gugcugcccu ggccuuugug    2460
cugcagcacc uccggcggcc cguggcccug cagcuggacu acaacucugu ggggugacauu    2520 ggcguggagc agcugcugcc uugccuuggu gucugcaagg cucuguauuu gcgcgauaac    2580
aauaucucag accgaggcau cugcaagcuc auugaaugug cuucacug cgagcaauug      2640 cagaaguuag cucuauucaa caacaaauug acugacggcu gugcacacuc cauggcuaag    2700
cuccuugcau gcaggcagaa cuucuuggca uugaggcugg ggaauaacua caucacugcc    2760
gcgggagccc aagugcuggc cgaggggcuc cgaggcaaca ccuccuugca guuccuggga    2820
uucuggggca acagaguggg ugacgagggg gcccaggccc uggcugaagc cuugggugau    2880
caccagagcu ugagguggcu cagccugguu ggaacaaca uggcagugu gggugcccaa      2940 gccuuggcac ugaugcuggc aaagaacguc augcuagaag aacucugccu ggaggagaac    3000
caucuccagg augaaggugu auguucucuc gcagaaggac ugaagaaaaa uucaaguuug    3060
aaaauccuga aguuguccaa uaacugcauc accuaccuag gggcagaagc ccuccugcag    3120
gcccuugaaa ggaaugacac caucuccggaa gucuggcucc gagggaacac uuucucucua   3180
gaggagguug acaagcucgg cugcaggac accagacucu gcuuugaag ucuccgggag     3240 gauguucguc cagguuuguu ugugagcagg cugugaguuu gggccccaga ggcugggguga   3300 cauguguugg cagccucuuc aaaaugagcc cuguccugcc uaaggcugaa cuuguuuucu    3360
gggaacacca uaggucaccu uuauucggc agaggaggga gcaucagugc ccuccaggau    3420
agacuuuucc caagccuacu uuugccauug acuucuuccc aagauucaau cccaggaugu    3480
acaaggacag ccccucccuc auaguauggg acuggccucu gcugauccuc ccaggcuucc    3540 gugugggguca gugggccca uggagugcu uguuaacuga gugccuuuug guggagaggc    3600
ccggccucuc acaaaagacc ccuuaccacu gcucugauga agaggaguac acagaacaca    3660
uaauucagga agcagcuuuc cccaugucuc gacucaucca uccaggccau ucccgucuc    3720 ugguuccucc ccuccuccug gacuccugca cacgcuccuu ccucugaggc ugaaauucag    3780
aauauuagug accucagcuu ugauauuuca cuuacagcac ccccaacccu ggcacccagg    3840
gugggaaggg cuacaccuua gccugcccuc cuuuccgggu uuaagacauu uuuggaagg    3900 ggacacguga cagccguuug uuccccaaga cauucuaggu uugcaagaaa aauaugacca    3960
cacuccagcu gggaucacau guggacuuuu auuccagug aaaucaguua cucuucaguu    4020
aagccuuugg aaacagcucg acuuuaaaaa gcuccaaaug cagcuuuaaa aaauuaaucu    4080
gggccagaau ucaaacggc cucacuaggc uucgguuga ugccugugaa cugaacucug     4140 acaacgacu ucugaaauag acccacaaga ggcaguucca uuucauuugu gccagaaugc    4200
uuuaggaugu acaguuaugg auugaaaguu uacaggaaaa aaaauuaggc cguuccuuca    4260
aagcaaaugu cuuccuggau uauucaaaau gauguauguu gaagccuuug uaaauuguca    4320
gaugcugugc aaaauguuau uauuuaaaca uuaugaugug ugaaacacgg uuuauauuua    4380
uaggucacuu uguuuuacug ucuuaaguuu auacucuuau agacaacaug gccgugaacu    4440
uuaugcugua aauaaucaga ggggaauaaa cuguugaguc aaaac                   4485
```

POLYMORPHISMS IN THE NOD2/CARD15 GENE

The present invention regards methods as well as nucleotide sequences used in these methods for prognosis and/or diagnosis of diseases associated with at least one of the polymorphisms Nod2-SNP8, Nod2-SNP12, Nod2-SNP13 in the NOD2/CARD15 gene and more particularly it regards the selection of suitable donor-recipient pairs for transplantations dependant on the identified polymorphisms Nod2-SNP8 (8), Nod2-SNP12 (12), Nod2-SNP13 (13) in the NOD2/CARD15 gene.

The single nucleotide polymorphisms (SNP) 8, 12, 13 in the NOD2/CARD15 gene are considered responsible for the incidence of Crohn's disease (Hugot J P, Chamaillard M, Zouali H, Nature 2001, 411, 599-603; Ogura Y, Bonen D K, Inohara N Nature 2001, 411, 603-606). Crohn's disease is a rare, but nonetheless devastating, chronically recurrent inflammation of the digestive tract mainly affecting the small and the large intestine. The intestinal wall is thickened and ulcers are caused.

It is the objective of the present invention to provide methods for the prognosis and diagnosis of diseases which may be caused or initiated by the mutations/variants Nod2-SNP8, Nod2-SNP12, Nod2-SNP13 in the NOD2/CARD15 gene. In particular, it is the objective of the invention to provide methods for predicting the likelihood of the incidence of graft-versus-host reactions, sepsis and other diseases occurring subsequently to transplantations, wherein the methods are used for selecting suitable donor-recipient pairs.

This objective is solved by providing methods according to claim 1. Further advantageous embodiments, aspects and details of the invention result from the dependant claims, the description, the examples and the figures.

The present invention relates to methods for the prognosis and/or diagnosis of diseases associated with at least one of the polymorphisms Nod2-SNP8, Nod2-SNP12, Nod2-SNP13 in the NOD2/CARD15 gene by detection of the presence of at least one of the polymorphisms Nod2-SNP8, Nod2-SNP12, Nod2-SNP13 in the NOD2/CARD15 gene.

In other words, the present invention regards methods for detecting at least one of the polymorphisms Nod2-SNP8, Nod2-SNP12, Nod2-SNP13 in the NOD2/CARD15 for the prognosis and/or diagnosis of diseases associated with this gene defect or respectively with a mutation or respectively with a gene variant.

The NOD2/CARD15 gene has the following Gene Bank Accession Number: AC007728 from the NCBI data base. The nucleotide sequence is available with the help of the given accession numbers from the NCBI data base at http://www.ncbi.nlm.nih.gov/.

The NOD2 gene has 3123 nucleotides (1040 amino acids, Gene Bank Accession Number NM_022162 (SEQ ID NO. 13)), (NOD: Nucleotide Oligomerisation Domain) and is located in the pericentromeric region of chromosome 16 (16p12-q21). In the meantime, the name of the gene NOD2 was changed to CARD15 (CARD: Caspase Activating Recruitment Domain). Caspases play an important role in apoptosis. In addition to the CARD domain, NOD2/CARD15 has a ATB binding domain. NOD2/CARD15 serves as intracellular receptor for bacterial products and transduces the signal for the activation of NFkappaB (NF-κB).

Among others, the single nucleotide polymorphisms (SNPs) Nod2-SNP8, Nod2-SNP12, Nod2-SNP13 may occur in the NOD2/CARD15 gene. SNPs are caused by a base exchange or insertion of an additional base into the DNA sequence.

SNP8 (SNP data base http://www.ncbi.nlm.nih.gov/SNP/index.html, Accession Number ss2978536) refers to a polymorphism in the NOD2/CARD15 gene resulting from the C→T exchange of the nucleotide in position 2209 (NM_022162). As a result, R702W is exchanged within the protein. SNP8 is located in chromosome 16 in chromosome position 50523959 (NOD2/CARD15 Gen-Exon 5). Hugot J P et al., Association of NOD2 leucine-rich repeat variants with susceptibility to Crohn's disease. Nature 2001, 411, 599-603.

SNP12 (SNP data base, Accession Number ss2978537) refers to a polymorphism in the NOD2/CARD15 gene resulting from the G→C exchange of the nucleotide in position 2827 (NM_022162). As a result, G908R is exchanged within the protein. SNP12 is located in chromosome 16 in chromosome position 50534573 (NOD2/CARD15 Gen-Exon 9). Hugot J P et al., Association of NOD2 leucine-rich repeat variants with susceptibility to Crohn's disease. Nature 2001, 411, 599-603.

SNP13 (SNP data base, Accession Number rs5743293) refers to a polymorphism in the NOD2/CARD15 gene resulting from one-base insertion of the nucleotide C in nucleotide position 3124 (NM_022162). SNP13 is located in chromosome 16 at the chromosomal position 50541811^50541812. The insertion results in a frameshift leading to a reduced NOD2 with 1007 amino acids (Ogura et al., Nature 2001, 411, 603-606).

The following 7 mutants/variants are caused by the above mentioned polymorphisms Nod2-SNP8, Nod2-SNP12, Nod2-SNP13:
mutant 1: mutation due to SNP8
mutant 2: mutation due to SNP12
mutant 3: insertion due to SNP13
mutant 4: mutation due to SNP8 and 12,
mutant 5: mutation and insertion due to SNP8 and 13,
mutant 6: mutation and insertion due to SNP12 and 13,
mutant 7: mutation and insertion due to SNP8, 12 and 13.

Surprisingly, it was found that already the presence of one of the aforementioned mutations is sufficient to cause various diseases. The mutations mentioned before are for example associated with rejection responses in transplant medicine, graft-versus-host diseases, host-versus-graft diseases, sepsis, lung diseases, monocyte dependent and/or macrophage dependent diseases, lymphoma, leukemia (acute lymphatic leukemia).

Monocyte dependant diseases are, among others, diseases caused by monocyte dysfunctions, such as, for example, monocytoses, inflammations of the heart valves, cirrhosis of the liver, monocytic leukemias, Morbus Hodgkin, Non-Hodgkin-lymphoma, chronic myeloid leukemia, multiple myeloma, malign histiocytosis, ovary tumors, stomach tumors, breast tumors, melanoma, Lupus erythematodes, rheumatoid arthritis, sarkoidosis, ulcerative colitis, Crohn's disease, Hand-Schuller-Christian-Syndrome. Accordingly, macrophage dependant diseases comprise diseases caused by a macrophage dysfunction. Among these are for example counted cardiovascular diseases. Among the lung diseases are for example chronic bronchitis and bronchiolitis obliterans.

Among the rejection responses in transplants are counted particularly immunological reactions of the recipient to the donor organ as well as graft versus host diseases (GvHD). Such consequences occur after a comparatively long period of time after a transplantation and may cause life-threatening complications.

This problem is to be further explained by means of the example of blood stem cell transplantation, commonly known as bone marrow transplantation. Particular examples for transplantations are spinal cord transplantations, bone marrow transplantations, stem cell and blood stem cell transplantations as well as transplantations of solid organs as for example heart, lung, liver, kidney, pancreas, skin, hormone producing glands as well as gonads.

The blood stem cell transplantation may be used for therapy of different disorders of hematopoiesis as well as disorders of the immune system, which may be caused, for example, by chemotherapies or other therapies with negative effects on hematopoiesis. Disorders of the immune system or of hematopoiesis, however, may also be inherent or acquired disorders. Problems regarding blood stem cell transplantation are particularly likely to occur if the donor is genetically not identical (allogenic donor), since in that case, a double immunological barrier has to be passed. Additionally to a possible rejection of the transplanted cells by the immune system of the recipient (HvG reaction), immunological reactions of the transplant against the recipient (GvH reactions) might occur.

The accordance of the HLA (human leukocyte antigen) haplotypes of donor and recipient is also a factor of significant importance as far as the likelihood of rejection responses is concerned.

Among others, the present invention discloses a further significant factor regarding the likelihood of rejection responses, namely the presence of at least one of the polymorphisms SNP8, SNP12 or SNP13 in the NOD2/CARD15 gene. The presence of at least one of these polymorphisms in both the recipient and the donor is particularly disadvantageous.

The graft versus host reaction (GvHR) caused by T-lymphocytes contained in the transplant of the donor may lead to a GvHD. GvHD may be acute or chronic. Per definition, the acute GvHD occurs within the first 100 days upon transplantation in up to 50% of the recipients of a transplant. Chronic GvHD occurs after day 100 in about 30-50% of the allogenic patients who underwent transplantation. According to the symptomatic and clinical laboratory values, GvHD can be subdivided in four stages (GvHD-I, GvHD-II, GvHD-III, GvHD-IV) with different prognoses.

Sepsis is a further severe and often lethal secondary disease occurring after transplantation which may be caused, for example, by bacteria transferred together with the graft. Every year, an estimated 100 000 people contract sepsis in Germany, for 40.000 of them the infection is lethal. Sepsis means that germs overwhelm the whole organism and intoxicate the blood, which may lead to a collapse of kidney, liver and lung. Sepsis is a killer disease caused by bacteria, fungi or viruses and may suddenly affect anyone.

Clinical studies proved that, surprisingly, sepsis occurs especially if both donor and recipient carry one of the polymorphisms SNP8, SNP12 and/or SNP13.

Furthermore, it was surprisingly found that already one of the prementioned mutations is sufficient to cause various diseases associated with a disorder of the NF-KB signal transduction pathway. A disorder of the NF-KB signal transduction pathway can mean both an inhibition and an activation. The diseases associated with a disorder of the NF-KB signal transduction pathway are thus initiated, caused, aggravated and/or triggered by an activation or inhibition of the NF-KB signal transduction pathway. Among these diseases are counted for example various types of cancer with mutations in the Rel/NF-kB/IkB genes as well as many other types of cancer with a hyperactivity and or a hyperexpression of NF-KB in the tumor cells. Among these diseases are furthermore cardiovascular diseases, heart diseases, diseases of the kidney, arteriosclerosis as well as atherosclerosis. The likelihood of an incidence of such diseases is significantly increased upon transplantations, if both recipient and donor carry at least one of the polymorphisms described herein.

The application of the methods according to the invention in pretransplantation diagnosis is particularly advantageous. The methods according to the invention allow a prognosis of response reactions of the recipient with regard to the donor organ as well as of graft versus host diseases (GvHD) and are therefore adequate for the selection of a suitable donor organ for a certain recipient. Response reactions occur particularly if both the recipient and the donor carry one of the mutations 1-7 mentioned above, a fact which will be further explained in detail below.

The methods according to the invention comprise the provision of a sample containing the NOD2/CARD15 gene and subsequent analysis of the NOD2/CARD15 gene for the presence of at least one of the mutations 1-7 described above. Preferably, genomic DNA or cDNA or RNA is used for the analysis.

Possible samples are blood, salvia/oral mucosa cells, bone marrow, urine sediment, punctuation liquid, cell and blood samples, wherein blood samples are preferred.

As far as pretransplantation diagnosis is concerned, it is also preferred to examine a sample of the recipient, as well as, separately, a sample of the donor. Thus, a diagnosis method is particularly preferred which helps to estimate the likelihood of the occurrence of graft versus host reactions comprising the following steps
  a) provision of a sample of the donor containing the NOD2/CARD15 gene as well as a sample of the recipient containing the NOD2/CARD15 gene,
  b) detection of the two samples for the presence of one or more of the polymorphisms Nod2-SNP8, Nod2-SNP12, Nod2-SNP13.

The following selection of suitable donor-recipient pairs occurs according to the principle of risk minimization as far as the likelihood of the occurrence of graft versus host reactions is concerned. If the recipient carries more than one polymorphism, i.e. if the recipient carries one of the mutations no. 4, 5, 6 or 7, the donor should be absolutely free of polymorphisms, i.e. carry none of the mutations 1-7. The risk that GvHD might occur is particularly high, if both donor and recipient carry a polymorphism and it is even increased if donor and recipient, together, carry more than two polymorphisms, e.g. if the donor carries the mutation 5 and if the recipient carries the mutation 1, or if the donor carries the mutation 4 and the recipient the mutation 6.

In a preferred embodiment, the method mentioned before comprises the following steps:
  a) providing a sample of the donor as well as of the recipient containing the NOD2/CARD15 gene,
  b) isolating DNA and/or RNA from both samples,
  c) performing separated polymerase chain reactions with specific primers for the NOD2/CARD15 gene for isolated DNA and/or RNA of the donor, as well as for the isolated DNA and/or RNA of the recipient
  d) examination of the donor's NOD2/CARD15 gene as well as of the recipient's NOD2/CARD1 5 gene for the presence of at least one of the polymorphisms Nod2-SNP8, Nod2-SNP12, Nod2-SNP13.

A preferred embodiment of the present invention relates to a method for estimating or respectively predicting rejection responses in the recipient after transplantation of cells or of an organ. In this method, a sample of the recipient and a sample of the donor are provided. The term "sample" is defined above and stands in particular for a blood sample. The donor's sample and the recipient's sample are examined for the presence of the polymorphisms SNP8, SNP12, SNP13. Preferably, the examination is carried out by means of isolation of DNA and/or RNA, preferably DNA, from both samples. In order to detect polymorphisms, the DNA and/or RNA isolated from the donor's sample are/is replicated by means of a PCR and subsequently charged with oligonucleotides with a complementary sequence to the polymorphisms SNP8 or SNP12 or SNP13 and capable of hybridizing with the section of the NOD2/CARD15 gene containing the polymorphisms Nod2-SNP8 or respectively Nod2-SNP12 or respectively Nod2-SNP13. Preferably, the oligonucleotides have between 10 and 50 nucleotide units (nucleobases). Three types of oligonucleotides are used, namely such with a complementary sequence to the section of the NOD2/CARD15 gene containing the SNP8 polymorphism as well as such with a complementary sequence to the section of the NOD2/CARD15 gene containing the SNP12 polymorphism and such with a complementary sequence to the section of the NOD2/CARD15 gene containing the SNP13 polymorphism. Occurrence of hybridization proves the presence of a polymorphism. The type of the hybridizing oligonucleotides shows which polymorphism is present and whether several polymorphisms are present. The PCR is performed with primers which are specific for the NOD2/CARD15 gene.

In order to replicate the DNA and/or RNA contained in the recipient's sample, it is subjected to a PCR and charged with the same oligonucleotides for the detection of polymorphisms.

The method according to the invention provides the information whether polymorphisms are present in the donor or in the recipient, or in the donor and in the recipient. Furthermore, it is possible to determine which and how many of the three polymorphisms are present. Depending on the result, the likelihood of rejection responses in the recipient of the graft may be estimated; thus suitable donor-recipient pairs can be selected and the risk of the incidence of secondary diseases due to transplantation is minimized.

Among the secondary diseases or immune reactions are particularly counted rejection responses upon transplantations, graft versus host diseases, host versus graft diseases, lung diseases, monocyte dependant and/or macrophage dependent diseases, lymphoma, leukemia and/or diseases associated with a disorder of the NFkappaB signal transduction pathway.

Experimental studies showed that the presence of one of the polymorphisms correlates with an increased incidence of rejection responses upon transplantations, graft versus host diseases, host versus graft diseases, sepsis, lung diseases, lymphoma, leukemia, monocytoses, inflammations of the heart valves, cirrhosis of the liver, monocytic leukemias, Morbus Hodgkin, Non-Hodgkin-lymphomas, chronic myeloid leukemia, multiple myeloma, malign histiocytosis, ovary tumors, stomach tumors, breast tumors, melanoma, Lupus erythematodes, rheumatoid arthritis, sarkoidosis, ulcerative colitis, Crohn's disease, Hand-Schuller-Christian-Syndrome, cardiovascular diseases, diseases of the heart, diseases of the kidney, arteriosclerosis, atherosclerosis, chronic bronchitis and bronchiolitis obliterans. The methods according to the invention lead to results allowing a statement regarding the likelihood of the incidence of the diseases mentioned before, in particular, the likelihood of an incidence of one or several of the prementioned diseases in the recipient after transplantation.

As described in detail above, after providing a sample containing the NOD2/CARD15 gene, the gene is examined for the presence of at least one of the mutations 1-7 mentioned above or respectively at least one of the polymorphisms 8, 12, 13. This examination can be performed according to several different methods, preferably comprising the isolation of DNA from the sample with subsequent PCR (Polymerase Chain Reaction) with primers which are specific for the NOD2/CARD15 gene.

Primers which may be used are for example the primers described in "THE LANCET", 2002, 359, 1661-1665.

The nucleotides obtained by the PCR may be examined for the presence of the mutations using various methods. Among these methods are for example: primer extension methods, mutation-specific hybridization, ARMS technologies, array technologies, chip technologies, DNA sequence analysis, restriction analysis (RFLP), single strand conformation polymorphism (SSCP) analysis, denaturing gradient gel electrophoresis, temperature gradient gel electrophoresis, denaturing HPLC, electrochemical detection methods. The measurement of hybridization signals of tagged hybridization sequences is particularly preferred.

Short Description of These Methods

Allele specific hybridization of fluorescently tagged DNA-probes (allele specific oligonucleotide (ASO) hybridization) is one method used in routine diagnosis for detecting known SNPs or mutations. This technique comprises the addition of a wild type specific and mutation-specific probe to the PCR, the fluorescence of which is only visible after decomposition of the probe, which at first is specifically bound, by the DNA polymerase during strand elongation (so called exonuclease assay). Depending on whether the wild type or an SNP/mutation is present, different color signals are obtained which are detected after stimulation by laser light in a photo cell. It is advantageous that this method may be partially automated, thanks to which a higher number of samples can be processed in a shorter period of time.

A more recent method for detecting known mutations or SNPs is pyrosequencing, a method developed in Sweden. Similar to classic DNA sequence analysis according to the Sanger method (see below), the DNA sequence can be directly analyzed by means of pyrosequencing. The reaction, however, is not due to the detection of fluorescence signals of integrated stop nucleotides, but to a measurable release of light when the respective, suitable nucleotide is inserted into the DNA during strand elongation. More particularly, hybridization sequences, i.e. oligonucleotides with complementary sequences, preferably carrying detection tags, are used for detecting the presence of a mutation.

A further method for analyzing known polymorphisms or SNPs is the detection of sequence-specific probes by means of LightCycler. Therein, a special reaction mixture containing, among others, primers and specific probes is added to a DNA template. For the detection of a SNP, a pair of probes consisting of an anchor probe and a sensor probe is required. Both probes bind in immediate proximity to each other to the sequence to be analyzed. After excitation of the fluorescein molecule on the anchor probe, an energy transfer to the LC-Red molecule at the sensor probe (fluorescence resonance transfer, FRET assay) takes place. The light emitted by the sensor probe is measured and indicates whether the probes are correctly bound to the target sequence. The genotype is determined by means of a melting curve analysis.

A method which is particularly suitable for the simultaneous detection of several known mutations (so called multiplex analysis) consists in the oligonucleotide ligation assay (OLA). The OLA is mainly used in step II (examination for the 31 most frequent mutations) of the CFTR diagnostic. 15 target sections of the CFTR gene are amplified in a multiplex PCR reaction. The PCR products from the multiplex PCR serve as starting molecules for a ligation reaction which is initiated by the addition of an OLA reagent. The OLA reagent contains oligonucleotides, which are partially fluorescently tagged, as well as a DNA ligase. 3 types of probes are used in the reaction: a) a common probe which is tagged with a fluorescent colorant (blue, green or yellow) at the 3' end, b) 29 probes which are specific for the wild type and c) 31 probes which are specific for the mutations. The common probe binds to the target sequence, independent of whether a wild type or mutant sequence is present. The wild type probes and mutation probes differ only in one nucleotide at the 3' end. A so called PEO molecule, the length of which is specific for each target sequence that is to be detected, is attached to the 5' end of wild type probes and mutation probes. The wild type and mutation probes compete for the binding site at the target sequence, wherein only that probe which is exactly complementary to the target sequence is able to bind. If none of the 31 mutations to be analyzed is found, only the wild type probes are bound. If a homozygous mutation is present, it's only the mutation probe which is bound. In the case of heterozygous mutations, both the wild type and the mutation probe bind to the target sequence. DNA ligase links the common wild type or mutation probe after hybridization to the target sequence. The ligation products can only be detected by capillary electrophoresis thanks to their specific length and different fluorescence tag of the common probe.

Thus, the present invention also relates to the oligonucleotides consisting of at least 10 nucleotide units, having a sequence complementary to the mutation SNP8 and/or SNP12 and/or SNP13 and being capable of hybridization with the section of the NOD2/CARD15 gene containing the polymorphism Nod2-SNP8 and/or Nod2-SNP12 and/or Nod2-SNP13.

Or respectively, the present invention regards oligonucleotides consisting of at least 10 nucleotides, wherein the oligonucleotides have a sequence which is complementary to the NOD2/CARD15 gene and contain the complementary nucleotides to the mutation SNP8 and/or SNP12 and/or the nucleotide insertion SNP13.

Such oligonucleotides preferably carry detection tags for the spectroscopic analysis or respectively for the fluorescent or chemiluminiscent based analysis. Furthermore, the oligonucleotides preferably consist of 15-50 nucleotide units and particularly preferred of 18-22 nucleotide units.

It is the objective of the present invention to furthermore provide a device for diagnosing the polymorphisms or respectively mutations of the NOD2/CARD15 gene. The device is preferably a diagnose chip or microchip containing at least one of the oligonucleotides mentioned before. In this microarray or microchip technology thousands of different genes in form of cDNA fragments or gene specific oligonucleotides are applied in high density to special carriers, mainly consisting of glass or nylon, with the help of robots (=DNA-chips).

RNA samples may also be used instead of the DNA-samples for the detection of the polymorphisms. The RNA based methods require, however, samples of cells which also express the NOD2/CARD15 gene.

DESCRIPTION OF THE FIGURES

FIG. 2 shows the HLA-identical sibling grafts; wt: n=55, mut n=23

FIG. 3 shows the HLA non related donor grafts; wt: n=61, mut; n=25

EXAMPLES

Figure 1:
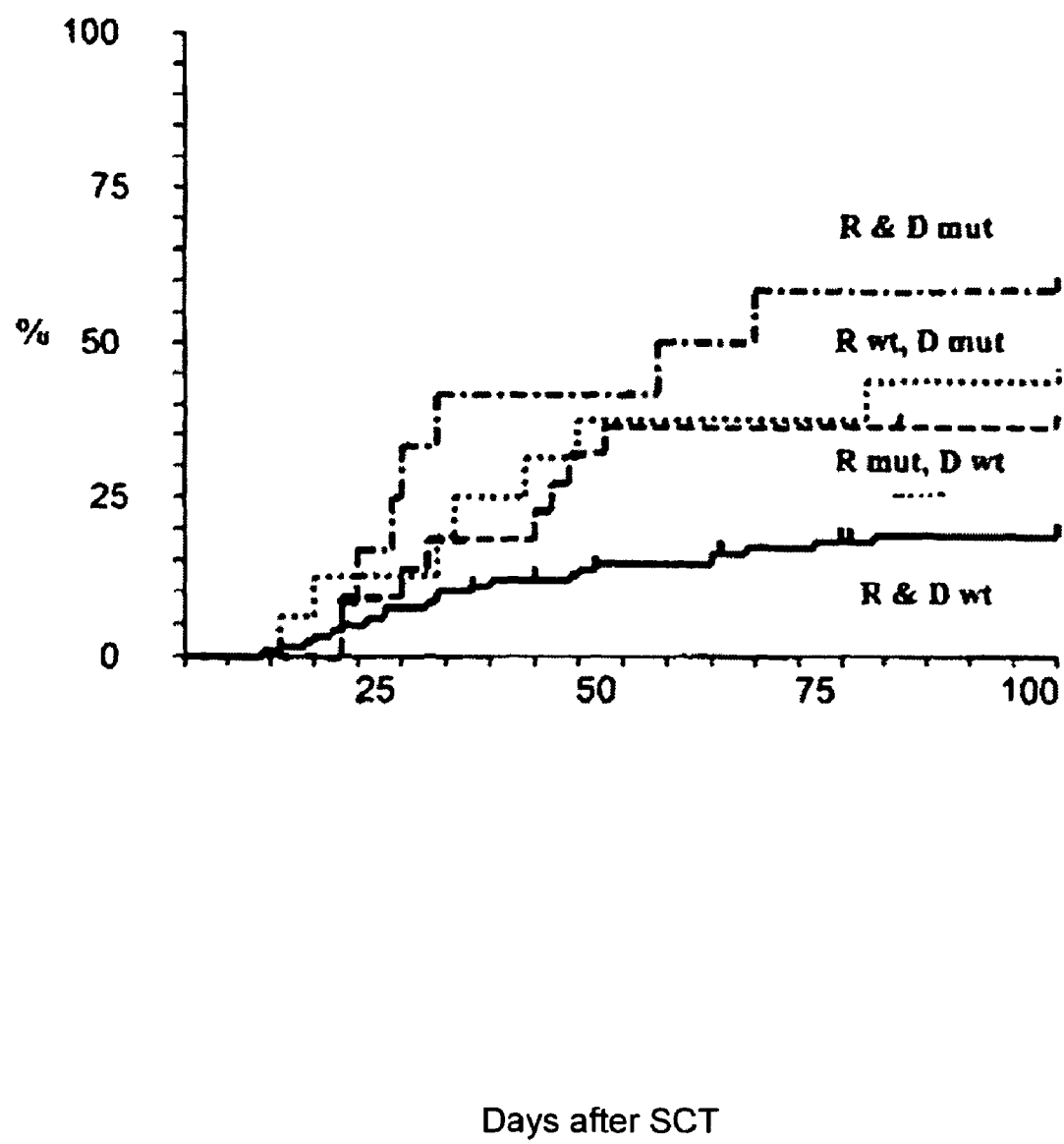
FIG. 1 shows the cumulative incidence of severe acute GvHD (grade III/IV) with reference to NOD2/CARD15 SNPs: R=recipient, D=donor; R & D wt=non-mutant wild type SNPs in R and D (n=119); R mut, D mut=mutant SNPs in recipients only (n=22); R wt, D mut=mutant SNPs in donors only (n=16), R & D mut=mutant SNPs in donor and recipient (n=12). The differences where highly significant: p 0.001 for all the groups; p 0.02 for R mut D wt; p 0.004 for R wt/D mut and p 0.001 for R & D mut, if no comparison to mutant R & D took place.

Methods 169 successive patients, which were hospitalized for allogenic stem cell transplantation, were included in the study. Conditioning and prophylactic immunosuppression were carried out according to standard protocols. Reduced intensity conditioning (RIC) consisted of fludarabine, BCNU and melphalan. 78 patients received transplants from HLA-identical siblings (matched related donors, MRD). 87 patients had no relations to the donors (URD, unrelated donors) and in 4 patients the donor was a relative, which had one different HLA antigen (RD). In the non related donor group, donor/recipient pairs matched regarding HLA, A, B, DRB1 and DQBL as was determined by a typization by means of low solution for class 1 and typization by high solution for class II. In the remaining 23 pairs one or two allele differences for DRB1 and DQB1 were accepted. The grade of GvHD was determined according to the Glucksberg criteria (Glucksberg H et al. Transplantation 1974, 18, 295-304). The main variables, such as graft related mortality (DIR=death in remission) and causes of death were entered in a monthly updated data base. The median observation time for surviving patients or for patients who died due to a relapse was 450 days (range of 30-1767 days), the median observation period for patients who died of DIR was 172 days (range of 14-1065 days).

Collection of DNA Samples

DNA from 169 patients (recipients) and from 168 donors was prepared from blood samples according to standard methods at the time of stem cell transplantation, frozen and analyzed retrospectively in order to determine the role of NOD2/CARD15 mutations.

Allelic discrimination of the NOD2/CARD15 gene

The single nucleotide polymorphisms NOD2-SNP8, NOD2-SNP12 and NOD2-SNP13 were determined by a Taq-Man protocol as described in Hampe et al. "THE LANCET", 2002, 359, 1661-1665.

Control samples, examined by DNA sequencing were included in each TaqMan run. Probes were covalently coupled with a reporter dye 6-FAM or TET at the 5' end and the quencher dye TAMRA was coupled to the 3' end of the probe. The primers and probes were synthesized by MWG Biotech (Ebersberg, Germany). The following primers and probes were used:

```
For NOD2-SNP8 polymorphism
Primer:  1)  5'TTCCTGGCAGGGCTGTTGTC 3'  (forward)
             (SEQ ID NO. 1)

2)  5'AGTGGAAGTGCTTGCGGAGG 3'  (reverse)
             (SEQ ID NO. 2)
```

-continued

```
Probe:   1) 5'FAM-CCTGCTCCGGCGCCAGGC-TAMRA 3'
            (SEQ ID NO. 3)

2) 5'TET-CCTGCTCTGGCGCCAGGC-TAMRA 3'
            (SEQ ID NO. 4)

For NOD2-SNP12 polymorphism
Primer:  1) 5'ACTCACTGACACTGTCTGTTGACTCT 3'
            (forward)
            (SEQ ID NO. 5)

2) 5'AGCCACCTCAAGCTCTGGTG 3' (reverse)
            (SEQ ID NO. 6)

Probe:   1) 5'FAM-TTTTCAGATTCTGGGGCAACAGAGTGG
            GT-TAMRA 3'
            (SEQ ID NO. 7)

2) 5'TET-TTCAGATTCTGGCGCAACAGAGTGGGT-
            TAMRA 3'
            (SEQ ID NO. 8)

For NOD2-SNP13 polymorphism
Primer:  1) 5'GTCCAATAACTGCATCACCTACCTAG 3'
            (forward)
            (SEQ ID NO. 9)

2) 5'CTTACCAGACTTCCAGGATGGTGT 3'
            (reverse)
            (SEQ ID NO. 10)

Probe:   1) 5'FAM-CCCTCCTGCAGGCCCTTGAAAT-
            TAMRA 3'
            (SEQ ID NO. 11)

2) 5'TET-CCTCCTGCAGGCCCCTTGAAA-
            TAMRA 3'
            (SEQ ID NO. 12)
```

The optimized reaction mixture with a final volume of 10 µl consisted of Universal Master Mix (PE Applied Biosystems), 400 nM of each primer (forward and reverse, see above), 250 nM of each fluorogenic probe (see above) and the DNA-matrix (20 ng/well). All reactions were carried out in a 384 well plate (Abgene, Epsom, UK) and amplified with the help of the thermocycler Primus HT (MWG Biotech). The conditions for the PCR cycles were as follows: 50° C. for 2 minutes, then 95° C. for 10 minutes followed by 40 cycles of 95° C. for 15 seconds (melting step) and 60° C. for 1 minute. After the PCR run, the released fluorescence was measured with the ABI PRISM® 7700 sequence detection system (PE Applied Biosystems, Forster City, Calif., USA).

The sequence detector (SDS version 1.6, PE Applied Biosystem) recorded increases regarding the amount of reporter dye fluorescence over the 40 cycles of the amplification. Changes in the reporter dye fluorescence of the 6-FAM versus changes in the reporter dye TET were determined graphically (homozygous FAM versus homozygous TET versus heterozygous FAM/TET).

Clinical and Statistical Analyses

Three main variables ( DIR at 365 days=1 year DIR, total grade of severe GvHD (grade III/IV) and stage of gastrointestinal GvHD) were analyzed with regard to NOD2/CARD 15 mutations. Cumulative incidence reflecting the competing risk of death of other toxicities or recurrence of GvHD and death incidences of recurrence for DIR were calculated for each of these parameters The period of time to the clinical event (DIR/GvHD) was measured from the due day of the SCT (stem cell transplantation) for total GvHD and gastrointestinal GvHD. The clinical events were included in the model up to day 100 and for one year DIR up to day 365 after SCT. Gradually multivariant COX regression models were adapted and tested the independent prognostic relevance of NOD2/CARD15 mutations. The limit for reverse selective procedures was the error likelihood of 0.2. For the multivariant comparison of risk factors for DIR and GvHD, only the age of the patients, disease stage at the day of transplantation, donor type (HLA identical siblings versus URD versus RD) and NOD2/CARD15 mutation status were reviewed. For the analysis of NOD2/CARD15 SNPs, the high risk alleles less frequently associated with Crohn's Disease and a limited NF-kB production were defined as mutated alleles, whereas the more frequently observed alleles were defined as wild types. For the analyses of the mutations with regard to the clinical event, the groups were formed according to 1) incidence of any kind of mutations in the recipient and in donors and 2) the incidence of any mutation in the recipient only, donor only or in both. Due to cumulative incidence competing risk could be taken into account, which was calculated with the help of NCSS software (version 2004); further statistical analyses were carried out with the help of the SPSS software (version 11.05).

Results:

Frequency of the Mutated NOD2/CARD15 Alleles:

NOD2/CARD15 mutations occurred with a frequency of 21.8% in patients and of 13.7% in donors involved in this study. A homozygous mutation was only observed in one patient and in his HLA-identical donor, whereas all the other patients and donors carrying mutations were heterozygous,. The calculated haplotype frequency for mutated NOD2-SNP8 was 0.056 for recipients (R) and 0.045 for donors (D); 0.021 (R) and 0.009 (D) for mutated NOD2-SNP12; and 0.027 (R) and 0.034 (D) for mutated NOD2-SNP13. Therefore, the haplotype frequencies were close to the range of the controls. This resulted in a total percentage of 70.5% of grafts with both donor and recipient having non-mutated SNPs (wild type group). In 22 pairs (13%), only the recipients carried mutated SNPs (R mut), in 16 pairs (9.5%) the mutations were observed only in donors (D mut), whereas in 12 pairs (7%) both donor and recipient had mutations (R & D mut). In our successive cohort of patients, both the donor-specific characteristics and the graft-specific procedures were equally distributed between patient/donor pairs with and without mutations.

Clinical Event with Regard to the Incidence of NOD2/CARD 15 Mutations in Donors and Recipients Patients were observed for a median of 16 months (range of 0.5 to 59 months). Firstly, we compared the event in patients of the wild type donor/recipient pair (n=119) with the event in patients of pairs with any kind of mutation (n=50). Generally, severe GvHD grade III/IV, severe gastrointestinal GvHD and DIR after 1 year in pairs with NOD2/CARD15 group significantly increased (see table 1) compared to the wild type. In both groups patients concerned by relapses died, 18 of the 119 patients of wild type pairs and 7 of the 50 patients of pairs carrying mutations.

There was an increased risk of severe total GvHD in grafts with donor mutations, when the mutation was classified according to the incidence in recipient or donor or in both. Additionally, the number of total and gastrointestinal GvHD in the small subgroups of pairs with mutations in both recipient and donor was drastically increased. As shown in table 2, the cumulative incidence of 1 year DIR was increased from 20 % in wild type recipient/donor pairs to 49% in pairs with a recipient mutation (p=0.03), to 59% in pairs with a donor mutation (p=0.004) and to 83% in pairs carrying a recipient and donor mutation (p=0.001). Again, mortality of patients concerned by recurrences were almost equally distributed in these subgroups.

The strong association of DIR with NOD2/CARD15 mutation was partially explained by an increased risk not only of death due to GvHD but also of respiratory failures as consequence of diffuse primary or secondary pulmonal disorders, whereas in the wild type group only 11/30 cases of death (37%) in remissions were caused by GvHD and respiratory failure. The percentage increased to 17/26 (65%) in pairs with NOD2/CARD15 mutations.

FIG. 1 and Table 2 show the cumulative incidence (cum. inc.) of severe acute GvHD (grade III/IV) with regard to NOD2/CARD15 SNPs. Compared to the wild type (19%), the cumulative incidence was increased to 36% or respectively 44% in the case of mutations either in the recipient or in the donor and to 58% in the case of mutations in both (R & D mut).

Relevance of the Observations for HLA-identical Siblings Compared to Non-related Donor Grafts and Multivariant Analysis of the Risk Associated with DIR.

Figure 2:
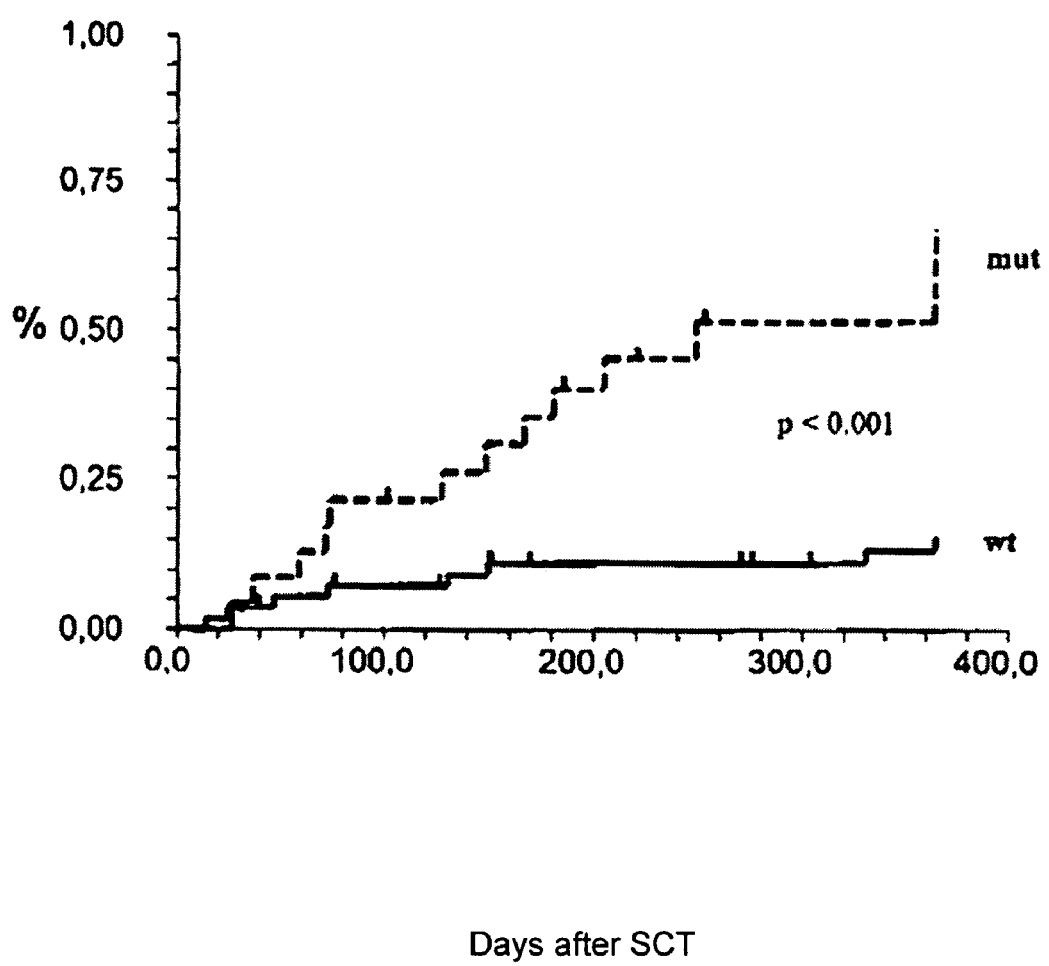
FIGS. 2+3 show the cumulative incidence of 1 year DIR with reference to the NOD2/CARD15 SNPs: wt=non-mutant SNPs both in recipients and donors; mut=any mutated SNP in donors or recipients or in both.

The relevance of donor and recipient mutation was compared in the different immunogenic subgroups involved in this study. Although the correlation of the incidence of DIR with NOD2/CARD 15 mutations was more obvious for the HLA-identical sibling grafts, a similar tendency could be observed for URD grafts (see FIG. 2, table 3). In the URD group the cumulative occurrence of 1 year DIR increased from 27% in wild type pairs to 55% in mutant pairs when the recipient and donor matched as far as HLA, A, B, DRB1 and DQB1 were concerned. DIR increased from 29% to 50% in pairs with one or two DRB1 or DQB1 allele differences.

The small group of grafts showing the antigen aberrances had a high mortality and thus the role of NOD2/CARD15 mutations in this special subgroup could not be assessed. In the multivariant Cox regression analysis, age, donor type and NOD2/CARD15 mutations in donors only or in both recipients and donors were independent risk factors for DIR. As shown in table 4, the hazard ratio for DIR after allogenic SCT regarding NOD2/CARD15 mutations was of 2.4 (p=0.02, 95 % Cl [1.1; 5.0]) for recipient mutations, 2.5 (p=0.02; 95 % Cl [1.2; 5.4]) for donor mutations and 6.0 (p=0; 95 % Cl [2.6; 14.1]) in the case of simultaneous mutations in both donor and recipient. GvHD (p=0.006) and NOD2/CARD15 mutations (p=0) remained significant risk factors for DIR, if the general GvHD grade IV was included as a risk factor for DIR in the model. Even if severe GvHD grade III/IV was included in the study, the distribution of the NOD2/CARD15 mutation remained significant, which confirmed the strong and independent effect of the NOD2/CARD 15 mutations on the course of disease (findings) after allogenic SCT.

TABLE 1

|  | Cumulative Incidence | 95% CI Cum. Inc. | p | HR | 95% CI HR |
|---|---|---|---|---|---|
| GvHD III/IV |  |  |  |  |  |
| Wild type | 19% | 13%-27% |  | 1.0 |  |
| mutant | 44% | 32%-60% | 0.001 | 2.7 | 1.5-4.9 |
| GI GvHD |  |  |  |  |  |
| Wild type | 18% | 12%-27% |  | 1.0 |  |
| mutant | 40% | 28%-56% | 0.004 | 2.5 | 1.4-4.7 |

TABLE 1-continued

|  | Cumulative Incidence | 95% CI Cum. Inc. | p | HR | 95% CI HR |
|---|---|---|---|---|---|
| DIR 1 year |  |  |  |  |  |
| Wild type | 20% | 14%-29% |  | 1.0 |  |
| mutant | 58% | 45%-75% | 0 | 2.8 | 1.7-4.9 |

Table 1 shows the univariant analysis of the cumulative incidence of acute GvHD grade III/IV, gastrointestinal GvHD stage 2-4 and 1 year DIR. Patient/donor pairs with non-mutated (wild type) NOD2/CARD15 (n=119) were compared to the pairs with recipient or donor mutations (mutated, n=50). Cox-regression was used to compare the groups and to analyze hazard ratios.

TABLE 2

|  | Cumulative Incidence | 95% CI Cum. Inc. | p | HR | 95% CI HR |
|---|---|---|---|---|---|
| GvHD III/IV |  |  |  |  |  |
| Wild type | 19% | 13%-27% |  | 1.0 |  |
| R pos | 36% | 21%-61% | 0.07 | 2.1 | 0.9-4.7 |
| D pos | 44% | 25%-76% | 0.002 | 2.8 | 1.2-6.5 |
| R & D pos | 58% | 36%-94% | 0.002 | 3.9 | 1.7-9.2 |
| GI GvHD |  |  |  |  |  |
| Wild type | 18% | 12%-27% |  | 1.0 |  |
| R pos | 36% | 21%-63% | 0.07 | 2.1 | 0.9-4.8 |
| D pos | 31% | 15%-65% | 0.16 | 2.0 | 0.8-5.3 |
| R & D pos | 56% | 36%-94% | 0.001 | 4.3 | 1.8-10.1 |
| DIR 1 year |  |  |  |  |  |
| Wild type | 20% | 14%-29% |  | 1.0 |  |
| R pos | 49% | 31%-76% | 0.03 | 2.2 | 1.1-4.6 |
| D pos | 59% | 38%-91% | 0.004 | 3.1 | 1.4-6.5 |
| R & D pos | 83% | 65%-100% | 0.001 | 3.9 | 1.7-8.6 |

Table 2 shows the detailed cumulative incidence for GvHD grade III/IV, gastrointestinal stage 24 and 1 year DIR with regard to donor and recipient NOD2/CARD15 mutations. Wild type non-mutated donors and recipients (n=119). R pos=mutation only in recipients (n=22), D pos=mutations only in donors (n=16); R & D pos=mutations both in recipients and in donors (n=12). Cox regression was used in order to compare the groups and to analyze hazard ratios.

Table 3 shows the univariant analysis of the cumulative incidence of 1 year DIR in patient/donor pairs with wild type NOD2/CARD15 compared to pairs with either recipient mutations (R pos) or donor mutations (D pos) as well as mutations in both (R & D pos). Separate analysis were carried out for HLA-identical sibling transplantation and URD grafts. The comparison between the groups was carried out with the log rank analysis. 95 Cl confidence intervals.

TABLE 3

|  | Cumulative Incidence | 95% CI Cum. Inc. | p | HR | 95% CI HR |
|---|---|---|---|---|---|
| HLA-id. sibl. |  |  |  |  |  |
| Wild type (55) | 14% | 18%-42% |  | 1.0 |  |
| R pos (9) | 74% | 49%-100% | 0 | 7.9 | 2.6-24.0 |
| D pos (6) | 58% | 27%-100% | 0.022 | 4.9 | 1.3-18.9 |
| R & D pos (8) | 75% | 50%-100% | 0.004 | 6.4 | 1.8-23.0 |

TABLE 3-continued

| | Cumulative Incidence | 95% CI Cum. Inc. | p | HR | 95% CI HR |
|---|---|---|---|---|---|
| URD | | | | | |
| Wild type (61) | 28% | 18%-42% | | 1.0 | |
| R pos (13) | 36% | 14%-73% | | 1.1 | 0.4-3.3 |
| D pos (9) | 31% | 13%-100% | | 2.4 | 0.9-6.5 |
| R & D pos (4) | 56% | 100% | 0.01 | 4.2 | 1.4-12.5 |

Table 4 shows the multivariant risk factor analysis for 1 year DIR. Relevant patient and donor pre-graft characteristics were compared to NOD2/CARD15 mutations in recipients (R pos), donors (D pos) and both (R & D pos).

TABLE 4

| | N | Incidence DIR 1 year | Risk | 95% CI | p |
|---|---|---|---|---|---|
| Age | | | | | |
| up to 40 years | 58 | 15 | 1.0 | | |
| from 40 years | 111 | 38 | 2.2 | 1.1-4.0 | 0.02 |
| Stage with Tx | | | | | |
| early | 95 | 27 | 1.0 | | |
| advanced | 74 | 26 | 1.3 | 0.7-2.2 | |
| Donor type | | | | | |
| HLA = sibl. | 78 | 20 | 1.0 | | |
| not related | 87 | 29 | 1.7 | 0.9-3.2 | |
| HLA df. rel. | 4 | 4 | 10.7 | 3.4-33.3 | 0 |
| NOD2/CARD15 | | | | | |
| Wild type | 119 | 26 | 1.0 | | |
| R pos | 22 | 10 | 2.4 | 1.1-5.0 | 0.02 |
| D pos | 16 | 9 | 2.5 | 1.2-5.4 | 0.02 |
| R & D pos | 12 | 8 | 6.0 | 2.6-14.1 | 0.001 |

The invention claimed is:

1. Method for predicting the likelihood of an incidence of a disease associated with at least one of the polymorphisms 8, 12, 13 in the NOD2/CARD15 gene by detecting at least one of the polymorphisms Nod2-SNP8, Nod2-SNP12, Nod2-SNP13 in the NOD2/CARD15 gene, wherein the disease associated with at least one of the polymorphisms 8, 12, 13 in the NOD2/CARD15 gene is graft versus host diseases.

2. Method according to claim 1 comprising the following steps:
   a) providing a sample containing the NOD2/CARD15 gene or respectively NOD2/CARD15 nucleic acids,
   b) examining the NOD2/CARD15 gene for the presence of at least one of the polymorphisms Nod2-SNP8, Nod2-SNP12, Nod2-SNP13.

3. Method according to claim 1 comprising the following steps:
   a) providing a sample containing the gene NOD2/CARD15,
   b) isolating DNA and/ or RNA from the sample,
   c) performing a PCR with specific primers for the NOD2/CARD15 gene,
   d) examining the NOD2/CARD15 gene for the presence of at least one of the polymorphisms Nod2-SNP8, Nod2-SNP12, Nod2-SNP13.

4. Method for predicting the likelihood of an incidence of a graft versus host disease according to claim 1 comprising the following steps:
   a) providing a sample of the donor containing the NOD2/CARD15 gene as well as a sample of the recipient containing the NOD2/CARD15 gene,
   b) detecting the two samples for the presence of one or more of the polymorphisms Nod2-SNP8, Nod2-SNP12, Nod2-SNP13.

5. Method according to claim 1, wherein at least one oligonucleotide consisting of at least 10 nucleotides is used, wherein the oligonucleotide has a sequence which is complementary to the NOD2/CARD15 gene and contains the complementary nucleotide to the mutation SNP8 and/or SNP12 and/or the nucleotide insertion SNP13.

6. Method according to claim 5, wherein the oligonucleotide furthermore contains a detection tag.

7. Method according to claim 1, wherein at least one microchip or chip for diagnosis is used within said method, wherein the microchip or chip for diagnosis contains at least one oligonucleotide consisting of at least 10 nucleotides, wherein the oligonucleotide has a sequence which is complementary to the NOD2/CARD15 gene and contains the complementary nucleotide to the mutation SNP8 and/or SNP12 and/or the nucleotide insertion SNP13.

8. Method according to claim 7, wherein the oligonucleotide furthermore contains a detection tag.

* * * * *